United States Patent [19]

Davidson et al.

[11] 4,440,782

[45] * Apr. 3, 1984

[54] METHOD OF TREATING VIRAL INFECTIONS

[75] Inventors: James P. Davidson, Lansing; Barnett Rosenberg, Holt, both of Mich.; Ronald W. Hinz, Avoca, Iowa

[73] Assignee: Research Corporation, New York, N.Y.

[*] Notice: The portion of the term of this patent subsequent to Mar. 24, 1998 has been disclaimed.

[21] Appl. No.: 188,343

[22] Filed: Sep. 18, 1980

Related U.S. Application Data

[62] Division of Ser. No. 773,216, Mar. 1, 1977, Pat. No. 4,258,051, which is a division of Ser. No. 540,109, Jan. 10, 1975, Pat. No. 4,053,587.

[51] Int. Cl.³ .................... A61K 31/28; A61K 31/555
[52] U.S. Cl. .................................. 424/287; 424/245
[58] Field of Search ............................. 424/287, 245

[56] References Cited

U.S. PATENT DOCUMENTS 4,140,707  2/1979  Cleare et al. .................... 424/287

OTHER PUBLICATIONS

Cleare et al., Platinum Metal Rev. 17, pp. 2–13, Mar. 8, 1973.

*Primary Examiner*—Jerome D. Goldberg
*Attorney, Agent, or Firm*—Scully, Scott, Murphy & Presser

[57] ABSTRACT

A method for treating animals afflicted with a viral infection comprising the administration to the animal of a platinum coordination compound.

3 Claims, No Drawings

METHOD OF TREATING VIRAL INFECTIONS

This application is a division of application Ser. No. 773,216, filed Mar. 1, 1977 now U.S. Pat. No. 4,258,051 which is a division of application Ser. No. 540,109, filed Jan. 10, 1975 now U.S. Pat. No. 4,053,587.

BACKGROUND OF THE INVENTION

Although there are many anti-bacterial agents available, very few comounds having in vivo anti-viral activity have been found acceptable to date.

It is an object of the present invention to provide a pharmaceutical composition and a method for treating viral infections in animals.

SUMMARY OF THE INVENTION

The present invention comprises a method for treating an animal afflicted with a viral infection comprising adminstering to the animal an effective amount of a platinum coordination compound.

According to a further aspect of the invention, there is provided a pharmaceutical composition in dosage unit form suitable for administration to an animal afflicted with a viral infection comprising a platinum coordination compound and an atoxic pharmaceutically acceptable carrier therefor.

DETAILED DESCRIPTION OF THE INVENTION

The anti-viral compound useful in the composition and method of the present invention are those having the formula:

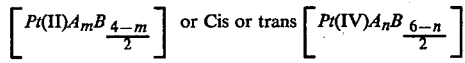

wherein "A" is a monodentate ligand, "B" is a bidentate ligand, m is 0, 2 or 4 and n is 0, 2, 4 or 6.

The monodentate ligands comprising "A" in the above structural formula may be any of those normally associated with platinum in its coordination compounds. For example, "A" may comprise Cl, Br, CN, NO$_3$, NH$_3$, H$_2$O, OH, OR, OS, etc., wherein R is the residue of an alcohol, preferably, an aliphatic alcohol.

The bidentate ligand (B) in the above structural formula may be any of those normally found in a platinum coordination compound. Suitable bidentate ligands include the aliphatic diamines, e.g., ethylenediamine, propylenediamine, butylenediamine, etc.

Among the preferred compounds are those wherein "A" is Cl, NH$_3$ or mixtures thereof and m is 4 and n is 6. These compounds are conventionally termed chloroplatinumammines. The most preferred chloroplatinumammines are cis-[Pt(II) (NH$_3$)$_2$Cl$_2$] and cis-[Pt(IV) (NH$_3$)$_2$Cl$_4$]. Also preferred are the aquoammine complexes such as cis-[Pt(II) (H$_2$O)$_2$NH$_3$)$_2$].

Also preferred among the platinum coordination compounds are those having the structural formula:

or

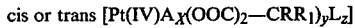

wherein:

X=1 or 2;
y=1 or 2;
z=0, 1 or 2,
provided that when y=2, z=0, and when y=1, z is greater than 0;
R and R$_1$ are selected from the group consisting of H, lower alkyl, aryl, aralkyl, alkenyl, cycloalkyl, cycloalkenyl, alkoxy, OH, or combine with the carbon atoms to form a cycloalkyl or cycloalkenyl group and substituted derivatives thereof:
when x=1, A is HR$_2$N—CHR$_3$—CHR$_4$—NR$_5$H and when x=2, A is H$_2$NR$_6$ a heterocyclic amine or an amino acid, wherein R$_2$, R$_3$, R$_4$ and R$_5$ are the same or different and are selected from the group consisting of H, CH$_3$, CH$_2$H$_5$, hydroxy and lower alkoxy, provided that R$_2$ and R$_5$ may also be aryl or aralkyl and each R$_6$ is the same or different and is selected from the group consisting of H, lower alkyl, aryl, aralkyl, hydroxy lower alkyl, hydroxyl- and alkoxyl-amines, alkoxy alkyl amines and heterocyclic substituents including said N as a ring member; all of said alkyl and alkoxy groups being lower alkyl and alkoxy groups.
when z=1, L is a bidentate anionc ligand, and when z=2, L is a monodentate anionic ligand.

In the above structural formulae, R and R$_1$ may comprise lower alkyl, (e.g., methyl, ethyl, n-propyl, isopropyl, n-butyl, etc.); aryl, (e.g., phenyl; lower alkyl-, lower alkenyl-, halo-, nitro-, lower alkoxy-substituted phenyl and naphthyl); aralykyl, (e.g., phenylmethyl (benzyl), 2-(1-napthyl)methyl); alkenyl, (e.g., 4-amino-1-butene, allyl); cycloalkyl, (e.g., cyclopropyl, cyclohexyl, etc.); cycloalkenyl, (e.g., 2-cyclopenten-1-yl, 2-cyclohexen-1-yl); alkoxy, (e.g., methoxy, ethoxy, etc.), and hydroxy. Also suitable are the 1,1-cycloalkylenedicarboxylic acids, (e.g., 1,1-cyclopropanedicarboxylic acid, 1,1-cyclobutane-dicarboxylic acid, etc.) and the 1,1-cycloalkenyldicarboxylic acids, (e.g., 1,1-cyclobutenedicarboxylic acid. etc.)

The malonato compounds of the above structural formula also contain two monodentate ammonia or primary or heterocyclic amine ligands, i.e., when x in the above formula is 2 or one bidentate amine ligand, i.e., when x is 1.

Suitable monodentate amine ligands include lower alkyl amines, (e.g., methyl-, ethyl-, n-propyl-, isopropyl-, n-butyl-amines, etc.), aryl amines, (e.g., aniline), aralkyl amines, (e.g., benzylamine), hydroxy lower alkyl amines, (e.g., ethanolamine, propanolamine, etc.), hydroxylamine, lower alkoxyl amines (e.g., methoxylamine, etc.), alkoxyalkylamines (e.g., methoxymethylamine, etc.), and heterocyclic amines (e.g., pyridine and aziridine). Also included are the amino acids, i.e., R$_7$—CHNH$_2$—COOH wherein R$_7$ is H, lower alkyl (e.g., methyl, isopropyl, etc.), hydroxy lower alkyl (e.g., hydroxymethyl, hydroxyethyl, etc.), aralkyl (e.g., benzyl, etc.).

It is to be understood that these coordination compounds may include two identical or different monodentate ligands.

Suitable bidentate amine ligands include the substituted and unsubstituted primary and secondary ethylenediamines. One or both of the carbon atoms of the ethylenediamine may contain substituents such as lower alkyl (e.g., methyl, ethyl), hydroxyl, alkoxy (e.g., methoxy, ethoxy, etc). Secondary ethylenediamines wherein one or more of the amine groups contains substituents such as listed above for the carbon atoms of the primary amine and aryl (e.g., phenyl) and aralkyl, (e.g., benzyl) may also be utilized.

The malonato Pt (IV) coordination compounds may also contain two monodentate or one bidentate anionic ligand where only one malonato ligand is present, i.e., where $y=1$ in the above formula.

Suitable monodentate anionic ligands include chloride, bromide, iodide, nitrite, hydroxide, nitrate, sulfamate, etc. Among the bidentate anionic ligands which may be present are oxalate, pyrophosphate, dithioxalate.

It is to be understood that the invention includes those coordination compounds containing mixed monodentate anionic ligands.

The preferred malonato compounds are those wherein R and $R_1$ in the above formula are H, methyl or ethyl, i.e., malonatoplatinum, methylmalonatoplatinum and ethylmalonatoplatinum coordination compounds. The most preferred Pt (II) compounds are those malonatoplatinum (II) compounds of the above formula wherein $x=1$ and $R_2$, $R_3$, $R_4$ and $R_5$ are each H, i.e., malonatoethylenediamine platinum (II), methylmalonatoethylenediamineplatinum (II) and ethylmalonatoethylenediamineplatinum (II); and wherein $x=2$ and each $R_6$ is H, i.e., malonatodiammineplatinum (II), methylmalonatodiammineplatinum (II) and ethylmalonatodiammineplatinum (II).

The preferred Pt (IV) compounds are those wherein $x=2$, each $R_6$ is H and $y=2$, i.e., bismalonato (or bismethylmalonato or bisethylmalonato) diammine platinum (IV); wherein $x=1$ and $R_2$, $R_3$, $R_4$ and $R_5$ are each H, $y=1$ or 2, $z=2$ and L is chloride, bromide, iodide or nitro and each $R_6$ is H.

The malonato compounds may be prepared by one of a variety of well known methods. A general method of preparation of the Pt (II) coordination compounds is as follows: Starting compounds having the formula cis-[Pt a(Hal)$_2$] wherein Hal is I, Cl or Br and A is one bidentate or two monodentate amine ligands (prepared by the method of S. C. Dhara, Indian J. Chem., Vol. 8, p. 193 (1970)) are reacted with silver nitrate to form the diaquo complex. The latter is then reacted with the malonate ion to form the coordination compounds of the invention. This method is represented by the following reaction scheme:

cis-[Pt ACl$_2$]+2AgNO$_3$+2H$_2$O→cis-[Pt A(H$_2$O)$_2$](NO$_3$)$_2$+2AgCl cis-[Pt A(H$_2$O)$_2$](NO$_3$)$_2$+H$_2$C—(COO)$_2$→[Pt A(OOC)$_2$—CH$_2$+2NO$_3$$^-$+2H$_2$O wherein A is one bidentate amine ligand or two monodentate amine ligands.

The other coordination compounds employed in the composition and method of the invention may be prepared according to methods well known in the prior art. See for example, Martel and Calvin, CHEMISTRY OF METAL CHELATE COMPOUNDS Prentice-Hall, Incorporated, Englewood Cliffs, New Jersey (1952); Bailar, THE CHEMISTRY OF COORDINATION COMPOUNDS, Reinhold Publishing Company, New York (1956); Dwyer and Mellar, CHELATING AGENTS AND METAL CHELATES, Academic Press, Incorporated, New York (1964); Kauffman, INORGANIC SYNTHESIS, Seven McGraw Hill Book Company Incorporated, New York (1963) and CHEMICAL ABSTRACTS, 44, 5257 g (1950).

The above-described platinum coordination compounds are also described in copending application Ser. Nos. 230,533 (filed Feb. 29, 1972; continuation of application Ser. No. 30,239; filed Apr. 20, 1970) and 260,989 (filed June 8, 1972). It is to be understood that the disclosures of these applications are incorporated herein by reference.

The pharmaceutical compositions of the invention may comprise the above-described platinum coordination compounds in admixture with suitable pharmaceutically acceptable carriers.

Where the composition is adapted for parenteral administration, the platinum coordination compounds may be dissolved or suspended in a suitable carrier liquid such as physiological saline, buffered saline, distilled water, peanut oil, etc. It will be understood that where the composition is intended for intravenous administration, the compounds must be in solution form and that where the compounds are intended for intramuscular or subcutaneous administration they may be in either solution or suspension form.

The platinum coordination compounds are effective against viral infections over a broad range of amounts depending upon the particular platinum coordination compound employed. Obviously, some of these compounds are more effective than others against such types of infections. Generally, however, for parenteral administration, dosages in the range of from about 0.1 to about 100 mg/kg. of body weight of the animal afflicted with the infection are generally effective. The most preferrred dosage range is from about 0.1 to about 10.0 mg/kg. of body weight.

Several of the above-described compounds have evidenced toxicity at the higher dosage levels in the above range. Thus, with respect to some of these compounds, some gastro-intestinal damage, bone-marrow depression or acute renal tabular necrosis may evidence itself at the higher dosage levels. It will be understood that toxicity levels for each compound may be easily determined by established testing methods and the dosages within the above-defined dosage ranges adjusted accordingly.

The following examples are illustrative of the invention:

EXAMPLE I

This example illustrates the inactivation of Rous Sarcoma Virus (BRYAN HIGH TITER STRAIN) with the associated helper virus RAV-1 in chick embryo fibroblast cells obtained from 15-I chickens which have been developed to be particularly sensitive to this virus. The tests set forth herein were done in tissue cultures. A stock suspension of the virus particles of known concentration was diluted and added to petri dishes in which the fibroblast cells had grown. After a predetermined time of incubation, the number of foci per plate was counted. In a second set of tests, the platinum compound, cis-dichlorodiammineplatinum (II), at a concentration of two parts per million was added to the bathing solution of the cells. This concentration was nontoxic to the fibroblast cells. Again, the number of foci were counted. The results are set forth in Table I in four repeat tests.

TABLE I

Anti-Viral Activity of cis-Dichlorodiammineplatinum (II)
Against Rous Sarcoma Virus: Tissue Culture Assay
Tissue: Chick Embryo Fibroblasts: Line 15-I Chickens
Concentration of cis-Pt(II) in treated plates = 2.0 ppm

| experiment Number | Conditions | Number of Foci per Plate | | | | |
|---|---|---|---|---|---|---|
| | | 1 | 2 | 3 | 4 | 5 |
| I | Control (RSV + RAV-1) | 15 | 20 | 12 | 15 | 16 |
| | RSV + RAV-1 + cis-Pt(II) | 10 | 8 | 5 | 5 | 5 |
| II | Control (RSV + RAV-1) | 10 | 9 | 9 | 14 | 22 |
| | RSV + RAV-1 + cis-Pt(II) | 5 | 6 | 15 | 16 | 6 |
| III | Control (RSV + RAV-1) | 17 | 17 | 10 | 15 | 11 |
| | RSV + RAV-1 + cis-Pt(II) | 10 | 9 | 9 | 2 | 0 |
| IV | Control (RSV + RAV-1) | 8 | 6 | 15 | 16 | 16 |
| | RSV + RAV-1 + cis-Pt(II) | 1 | 0 | 0 | 7 | 4 |

Mean number of Foci/Control Plate = 13.7
Mean number of Foci/Treated Plate = 6.15
% Decrease = ~50%.

It is apparent from the results set forth in Table I that the presence of the platinum coordination compound caused a marked decrease (approximately 50%) in the number of foci per plate. This reflects an inactivation of the Rous virus in a tissue culture system.

EXAMPLE II

The test described herein represents an in vivo test of the platinum coordination compound. Employed as an assay system were 7-8 day old 15-I chickens. All birds were innoculated in the wing web with one half ml stock viral suspension containing $10^4$ Rous Sarcoma Virus particles and associated helper virus, RAV-1. In Table II, the controls in the 4 experiments show that in all chickens employed, the virus caused the development of a Sarcoma tumor at the site of innoculation. There was 100% take of these tumors. In each experiment set forth in Table II, the treated birds were injected simultaneously with 4 mg/kg of cis-dichlorodiammineplatinum (II) in saline solution at the same time and at the same site.

TABLE II

Anti-Viral Activity of cis-Dichlorodiammineplatinum (II)
Against Rous Sarcoma Virus: In Vivo Assay
7-8 day old 15-I Chickens
All birds inoculated with 0.5 ml. containing $10^4$ particles
RSV + RAV-1 in the wing web.
Treated birds given 4 mg/kg cis-Pt(II) simultaneously in inoculum.

| Experiment Number | Conditions | Number of Birds | Results |
|---|---|---|---|
| 1 | Control | 6 | 6 positive |
| | Treated | 20 | 4 negative |
| | | | 16 positive |
| 2 | Control | 6 | 6 positive |
| | Treated | 20 | 6 negative |
| | | | 14 positive |
| 3 | Control | 7 | 7 positive |
| | Treated | 20 | 2 negative |
| | | | 18 positive |
| 4 | Control | 6 | 6 positive |
| | Treated | 20 | 3 negative |
| | | | 17 positive |

The results in Table II show that between 15 and 20% of the birds did not develop a Sarcoma in the wing web. This test indicates the effectiveness of cis-Dichlorodiammineplatinum (II) in causing a marked decrease in the tumor incidence due to the Rous Sarcoma Virus in the chicken in this In Vivo Assay system.

EXAMPLE III

A pool of Fowl Pox Virus had been previously prepared and assayed for the number of viral particles by the standard technique. For the tests herein, a glass vial containing a 2 ml frozen aliquot of fowl pox virus from the stock solution was placed in tepid water, allowing the virus suspension to thaw rapidly. The sample was diluted to $0.5 \times 10^{-3}$ dilution using sterile distilled water, prechilled to about 2° C., as the diluent. This final solution contained approximately 150 viable virus particles per ml and was maintained at 2° C. in an icewater bath during the course of the experiment.

Freshly embryonated eggs from white leghorn hens were incubated at 37° C. for ten days in a commercial, automatic turning poultry incubator. The eggs were then transferred to a box type incubator requiring hand turning and maintained at 37° C. through the nineteenth day, which was the termination date for the experiment.

On the thirteenth day of embryonation, an artificial air cell was prepared on the chorioallantoic membrane (CAM) of each egg using a standard technique developed by Cunningham.* Shell holes were temporarily sealed with masking tape and all eggs returned to the incubator.

*Charles H. Cunningham, A Laboratory Guide in Virology, Method 3, pages 29–32, 6th Edition.

Solutions of cis-diaquodiammineplatinum (II) were prepared in sterile distilled water to contain 0.0195 mg/ml. The solution was stored in the dark between inoculations. 0.1 ml of the virus dilution was inoculated onto the CAM of each egg at the location of the artificial air cell. The time of inoculation was noted. At a selected time interval (0, 1, 2, 4, 6, 8, 10 or 24 hours) following introduction of the pox virus, 0.2 ml of the platinum solution was inoculated onto the CAM in the same site that had previously received the virus. The shell holes were sealed with molten paraffin and the eggs returned to the incubator where they were placed on their sides so that the artificial air cell was uppermost.

A similar number of control eggs received 0.2 ml of sterile distilled water as a substitution for the platinum treatment. Identical time intervals were used following viral inoculation.

Eggs were candled daily for the first two days following the inoculation procedure. Those eggs found dead during this period were considered to have been killed by the technique as opposed to the virus or the platinum coordination compound and were discarded.

On the fifth to sixth day of incubation following infection with the virus, the eggs were opened and the CAM carefully extracted. After two rinses in tap water, the pox lesions present on the membrane were counted. Any necrotic, erosive or ulcerative lesions in the area of the artificial air cell were also noted.

The results of these two sets of experiments are shown in Tables III and IV. In Table III, the time of treatment was extended only to four hours after the virus inoculation.

TABLE III

Anti-Viral Activity of cis-Diaquodiammineplatinum (II)
Against Fowl Fox Virus: In Vivo
Embryonated White Leghorn Eggs
3.9 micrograms cis-Pt(II)(NH$_3$)$_2$(H$_2$O)$_2$ in 0.2 ml. water per egg

| Delay Time (hours) Between Virus & Pt | Pox Lesions/egg | Mean Lesions/egg |
|---|---|---|
| 0 Virus + Pt | 1,0,0,0,0,1,0,3,0 | 0.56 |

TABLE III-continued

Anti-Viral Activity of cis-Diaquodiammineplatinum (II)
Against Fowl Fox Virus: In Vivo
Embryonated White Leghorn Eggs
3.9 micrograms cis-Pt(II)(NH$_3$)$_2$(H$_2$O)$_2$ in 0.2 ml. water per egg

| Delay Time (hours) Between Virus & Pt | Pox Lesions/egg | Mean Lesions/egg |
|---|---|---|
| Virus + H$_2$O | 4,6,20,10,12,8,9,11,0 | 8.89 |
| 1 Virus + Pt | 4,0,0,6,1,1,3,1,0 | 1.78 |
| Virus + H$_2$O | 11,15,30,8,23,14,18,19 | 17.25 |
| 2 Virus + Pt | 2,1,2,2,1,1,0,1,2,2 | 1.40 |
| Virus + H$_2$O | 19,18,13,14,5,18,12,8 | 13.38 |
| 4 Virus + Pt | 6,2,2,2,1,2,8,2,3,2 | 3.00 |
| Virus + H$_2$O | 10,21,24,8,16,8,13,20,25 | 16.11 |

TABLE IV

Anti-Viral Activity of cis-Diaquodiammineplatinum (II)
Against Fowl Pox Virus: In Vivo
Embryonated White Leghorn Eggs
3.9 micrograms cis-Pt(II)(NH$_3$)$_2$(H$_2$O)$_2$ in 0.2 ml. water per egg

| Delay time (hours) Between Virus & Pt | Pox Lesions/egg | Mean Lesions/egg |
|---|---|---|
| 0 Virus + Pt | 0,0,1,0 | 0.25 |
| Virus + H$_2$O | 7,4,11,13 | 8.75 |
| 2 Virus + Pt | 0,0,1,3,0 | 0.80 |
| Virus + H$_2$O | 20,9,9,12,10 | 12.00 |
| 4 Virus + Pt | 0,1,2,1,0 | 0.80 |
| Virus + H$_2$O | 12,10,23,7 | 13.00 |
| 6 Virus + Pt | 0,4,2,2,4 | 2.40 |
| Virus + H$_2$O | 15,8,2,17,13 | 11.00 |
| 8 Virus + Pt | 0,1,1,3,1 | 1.20 |
| Virus + H$_2$O | 6,30,11,8 | 13.75 |
| 10 Virus + Pt | 4,5,1,0,7 | 3.40 |
| Virus + H$_2$O | 9,7,6,18 | 10.00 |
| 24 Virus + Pt | 10,10,9,7,12 | 9.60 |
| Virus + H$_2$O | 9,18,10,18,8 | 12.60 |

It is apparent from the results of Tables III and IV that the number of pox lesions was greatly decreased by the treatments with the platinum coordination complexes.

The percentage reduction in the number of lesions is a function of the time interval between virus inoculation and platinum compound. The percentage reductions for the experiments in Tables III and IV are shown in Tables V and VI, respectively.

TABLE V

Percent Reduction in Mean Number of Pox Lesions for Different Delay Times Between Virus Inoculum and Pt Treatment

| Delay Time | % Reduction |
|---|---|
| 0 | 93.7 |
| 1 | 89.7 |
| 2 | 89.5 |
| 4 | 81.4 |

TABLE VI

Percent Reduction in Mean Number of Pox Lesions for Different Delay Times Between Virus Inoculum and Pt Treatment

| Delay Time | % Reduction |
|---|---|
| 0 | 97.2 |
| 2 | 93.3 |
| 4 | 93.8 |
| 6 | 78.2 |
| 8 | 91.3 |
| 10 | 66.7 |
| 24 | 23.7 |

The results of the above experiments clearly indicate that the platinum coordination compounds are potent inhibitors of viral infections in an in vivo system even up to 24 hours after the virus infection.

What is claimed is:

1. A method for treating an animal afflicted with a viral infection comprising administering to said animal an effective anti-viral amount of a platinum coordination compound having the formula:

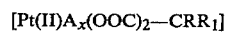

[Pt(II)A$_x$(OOC)$_2$—CRR$_1$]

wherein:

x = 1 or 2;

R and R$_1$ are selected from the group consisting of H, lower alkyl, aryl, aralkyl, alkenyl, cycloalkyl, cycloalkenyl, alkoxy, OH, or combine with the carbon atom to form a cycloalkyl or cycloalkenyl;

when x = 1, A is HR$_2$N—CHR$_3$—CHR$_4$—NR$_5$H and when x = 2, A is H$_2$NR$_6$ or an amino acid, wherein R$_2$, R$_3$, R$_4$ and R$_5$ are the same or different and are selected from the group consisting of H, CH$_3$, C$_2$H$_5$, hydroxy and lower alkoxy, provided that R$_2$ and R$_5$ may also be aryl or aralkyl and each R$_6$ is the same or different and is selected from the group consisting of H, lower alkyl, aryl, aralkyl, hydroxy lower alkyl, hydroxyl- and alkoxylamines, and alkoxyl alkyl amines, all of said alkyl and alkoxy groups being lower alkyl and alkoxy groups.

2. A method according to claim 1 wherein the amount of said compound administered is from about 0.1 to about 100 mg/kg of body weight of said animal.

3. A method according to claim 1 wherein said compound is administered parenterally.

* * * * *